United States Patent [19]
Bardelli et al.

[11] Patent Number: 5,893,382
[45] Date of Patent: Apr. 13, 1999

[54] METHOD AND DEVICE FOR FLUSHING A MEMBRANE APPARATUS

[75] Inventors: Francesco Bardelli, Medolla; Anna Puppini, Concordia, both of Italy

[73] Assignee: Hospal AG, Basel, Switzerland

[21] Appl. No.: 08/776,311

[22] PCT Filed: May 30, 1996

[86] PCT No.: PCT/IB96/00530
§ 371 Date: Apr. 8, 1997
§ 102(e) Date: Apr. 8, 1997

[87] PCT Pub. No.: WO96/38189
PCT Pub. Date: Dec. 5, 1996

[30] Foreign Application Priority Data

May 30, 1995 [IT] Italy ................ TO95A0442

[51] Int. Cl.$^6$ ............ B08B 3/10; B08B 9/00; B08B 9/093
[52] U.S. Cl. .......... 134/22.12; 134/22.1; 134/22.18; 134/169 R
[58] Field of Search ............ 134/22.12, 22.18, 134/22.1, 166 R, 169 R

[56] References Cited

U.S. PATENT DOCUMENTS 4,324,663  4/1982  Hirel et al. ................ 210/646
4,900,152  2/1990  Wiegleb ................ 356/411
4,923,613  5/1990  Chevallet ................ 210/647
5,004,548  4/1991  Richalley et al. ................ 210/646
5,041,215  8/1991  Chamberlain, Jr. et al. ........... 210/136

FOREIGN PATENT DOCUMENTS 0 186 973 A2  7/1986  European Pat. Off. .
0 291 421 A1  11/1988  European Pat. Off. .
0 543 172 A2  5/1993  European Pat. Off. .
27 34 075 A1  2/1978  Germany .
2 052 303  1/1981  United Kingdom .
WO 93/00938  1/1993  WIPO .
WO 97/02057  1/1997  WIPO .

*Primary Examiner*—Zeinab El-Arini
*Attorney, Agent, or Firm*—Finnegan, Henderson, Farabow, Garrett & Dunner, L.L.P.

[57] ABSTRACT

A method and apparatus are disclosed for flushing a blood treatment apparatus. The blood treatment apparatus has a first compartment and second compartment separated by a semipermeable membrane substantially impermeable to gas. A flushing circuit is set up by connecting an inlet of the blood treatment apparatus to a flushing liquid source and an outlet of the blood treatment apparatus to a discharge pipe. Liquid is circulated through the flushing circuit in pressure waves. These pressure waves dislodge air bubbles adhering to an inner wall of the blood treatment apparatus and discharge the air bubbles in the flushing liquid.

12 Claims, 2 Drawing Sheets

METHOD AND DEVICE FOR FLUSHING A MEMBRANE APPARATUS

This is a national stage application of PCT/IB96/00530 filed May 30, 1996.

BACKGROUND OF THE INVENTION

1. Field of the Invention

The present invention relates to a method and a device for the initial flushing of a blood treatment apparatus.

2. Description of the Related Art

It is known that before commencing dialysis treatment, the dialyser has to be flushed and filled (procedure referred to as priming) by passing a flushing solution through the compartments of the dialyser. Various methods have been proposed for carrying out this flushing. For example, U.S. Pat. No. 5,004,548 describes a method which consists in connecting the outlet of the dialyser's blood compartment to the inlet of the dialysis liquid compartment, and in circulating in series, through the blood compartment and the dialysis liquid compartment, a sterile physiological saline solution issuing from a bag. The outlet of the dialysis liquid compartment is connected to a bag for collection and discharge of the flushing liquid.

In a known flushing method, the flushing liquid is not recovered in a collecting bag, but is eliminated via the dialysis apparatus' pipes for discharge of used liquid. For this purpose, the outlet connection piece of the dialysis liquid compartment is connected, by way of a conduit and an electromagnetic valve, to a discharge pipe provided in the dialysis apparatus in proximity to the outlet of an ultrafilter. At the same time, a dialysis liquid is circulated through the ultrafilter, so that the liquid for flushing the dialyser and the dialysis liquid in preparation are thus discharged together in the discharge pipe.

The advantage of this solution is that it permits considerable savings to be made, by omitting the collecting bag and avoiding the expenses involved in disposing of the latter, and it permits an improvement in the flushing of the dialyser. In addition, there is no risk of the dialyser or of the sterile parts of the apparatus being contaminated by the non-sterile liquid since there is complete separation of the sterile and non-sterile parts of the apparatus.

To ensure satisfactory flushing of the dialyser, any air bubbles present on the membrane of the dialyser have to be eliminated. To do this at the present time, the person charged with performing the dialysis gently taps the dialyser so that the bubbles dislodge from the membrane and are discharged with the flushing liquid.

An object of the invention is to perfect the flushing method indicated above, in such a way as to render it completely automatic, while at the same time retaining the advantages of the known flushing method described hereinabove.

SUMMARY OF THE INVENTION

To achieve this object, the invention provides a method for flushing a blood treatment apparatus, which has a first compartment and second compartment separated by a semipermeable membrane, consisting in:

setting up a flushing circuit by connecting an inlet of one compartment to a flushing liquid source, and an outlet of this compartment to discharge means;

circulating flushing liquid through the flushing circuit;

the method being characterized in that it consists in creating pressure waves at time intervals in the flushing circuit in such a way as to dislodge air bubbles adhering to an inner wall of the blood treatment apparatus and to discharge these air bubbles in the flushing liquid.

According to one characteristic of the invention:

the flushing liquid is made to circulate by pumping means arranged on the flushing circuit on the inlet side (or outlet side, respectively) of the compartment; and in that the pressure waves are created by alternately opening and closing occlusion means which are arranged on the flushing circuit on the outlet side (or inlet side, respectively) of the compartment.

In one embodiment of the invention, the opening and closing of the occlusion means are controlled as a function of a pressure Pi measured in a flushing circuit section located between the pumping means and the occlusion means.

In another embodiment of the invention, the opening and closing of the occlusion means are controlled in accordance with a predetermined time sequence.

The invention also provides a device for flushing a blood treatment apparatus, which has a first compartment and second compartment separated by a semi-permeable membrane, this device comprising a flushing circuit which has:

means for supplying flushing liquid to at least one compartment;

pumping means for circulating the flushing liquid through the flushing circuit;

means for discharging the flushing liquid which has been used;

characterized in that it comprises means for creating pressure waves at time intervals in the flushing circuit in such a way as to dislodge air bubbles adhering to an inner wall of the blood treatment device and to discharge these air bubbles in the flushing liquid.

According to one characteristic of the invention, the means for creating pressure waves comprise:

occlusion means for selectively prohibiting the circulation of liquid in the flushing circuit, these occlusion means being situated downstream (or upstream, respectively) of the membrane apparatus, while the pumping means are situated upstream (or downstream, respectively) of the membrane apparatus;

control means for controlling the opening and closing of the occlusion means in such a way as to create pressure waves in the flushing circuit.

In one embodiment of the invention, the control means are intended to control the opening and closing of the occlusion means as a function of the pressure measured in a section of the flushing circuit located between the pumping means and the occlusion means.

In another embodiment of the invention, the control means are intended to control the opening and closing of the occlusion means in accordance with a predetermined time sequence.

Other advantages and characteristics of the invention will become evident on reading the description of a preferred embodiment of the invention, this description being given by way of non-limiting example and with reference to the attached drawings, in which:

DESCRIPTION OF THE PREFERRED EMBODIMENTS

Figure 1:
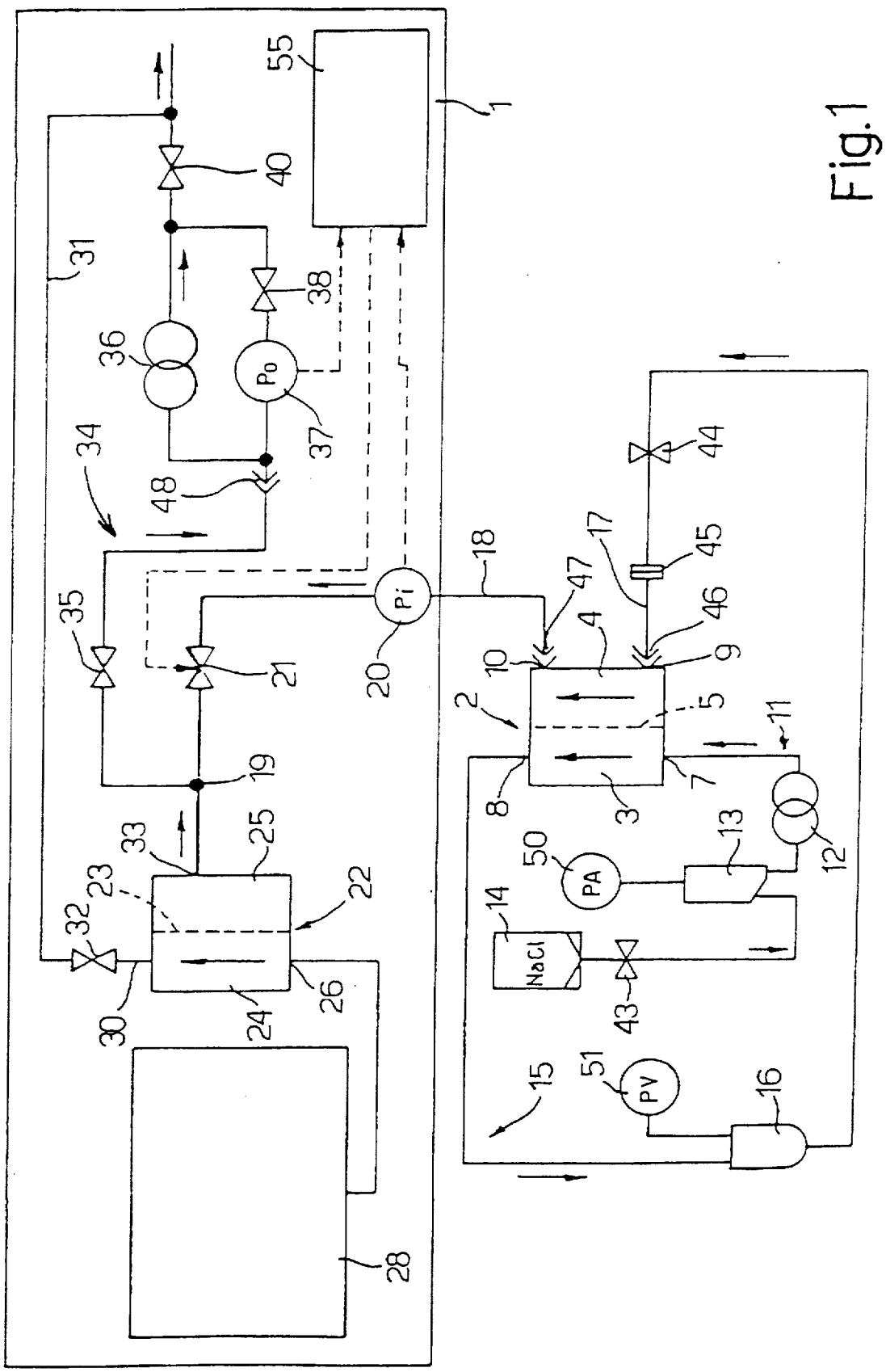
FIG. 1 is a diagrammatic representation of the hydraulic circuit of a dialysis machine.

FIG. 1 is a diagrammatic representation of the hydraulic circuit of a dialysis machine 1 connected to a dialyser 2 for the flushing procedure. The connection pieces and the elements which do not play a part in the flushing method according to the invention have been omitted in the figure.

The dialyser 2 comprises a blood compartment 3 and a dialysis liquid compartment 4 which are separated by a semi-permeable membrane 5. The blood compartment 3 has an inlet 7 and an outlet 8; the dialysis liquid compartment 4 has an inlet 9 and an outlet 10. The inlet 7 of the blood compartment 3 is connected to a bag 14 of flushing liquid (sterile physiological saline solution) by means of an arterial line 11 equipped with a peristaltic pump 12 (blood pump) and an expansion chamber 13; the outlet 8 of the blood compartment is connected to the inlet 9 of the dialysis liquid compartment by means of a venous line 15 equipped with a bubble trap 16 and a pipe section 17. The outlet 10 of the dialysis liquid compartment is connected to the outlet of an ultrafilter 22 (junction point 19) by means of a connecting pipe 18 equipped with a sensor 20 for pressure Pi and with an electromagnetic valve 21.

The ultrafilter 22 is divided by a semi-permeable membrane 23 into two chambers: an inlet chamber 24 and an outlet chamber 25. The inlet chamber 24 has an inlet 26 connected to a unit 28 for preparation of dialysis liquid, and an outlet 30 connected to a branch pipe 31 equipped with an electromagnetic valve 32. The outlet chamber 25 has an outlet 33 connected to the connecting pipe 18 and to a discharge pipe 34.

The discharge pipe 34 includes a first pipe section and a second pipe section which are linked via a connection piece 48. The first section, which is connected directly to the outlet 33 of the ultrafilter 22, is equipped with a first electromagnetic valve 35. The second section is equipped with a gear pump 36 and with a second electromagnetic valve 40. A pipe section equipped with a pressure sensor for P0 and with a third electromagnetic valve 38 is arranged bypassing the pump 36.

The branch pipe 31, one end of which is connected to the outlet 30 of the first chamber of the ultrafilter 22, is connected at its other end to the discharge pipe 31, downstream of the second electromagnetic valve 40.

FIG. 1 also shows diagrammatically various clamps and various connection pieces on the tubing. In particular, on the arterial line 11, between the blood pump 12 and the bag 14, there is a clamp 43, and an analogous clamp 44 is arranged on the venous line 15 downstream of the bubble trap 16. A connection piece 45 is provided in order to connect the venous line 15 to the pipe section 17; a connection piece 46 is provided in order to connect the pipe section 17 to the inlet 9 of the dialysis liquid chamber of the dialyser 2; a connection piece 47 is provided in order to connect the outlet 10 of the dialysis liquid chamber 4 to the connecting pipe 18; and the connection piece 48 arranged on the discharge pipe 34 is provided in order to connect the second section of the discharge pipe 34 to the inlet 9 of the dialysis liquid chamber, at the end of the flushing procedure, so as to proceed with dialysis.

A sensor 50 for arterial pressure AP is connected to the expansion chamber 13, and a sensor 51 for venous pressure VP is connected to the bubble trap 16.

The valve 21 on the connecting pipe 18 has the function of ensuring total protection of the dialyser 2 from any contamination of the dialysis liquid during the flushing operation. The valve 21 is activated in such a way that the pressure in the connecting pipe 18 always remains greater than the pressure in the discharge pipe 34, and in such a way that the dialysis liquid being prepared cannot flow back towards the dialyser 2. To this end, the pressures Pi and P0, measured by means of the pressure sensors 20, 37 in the connecting pipe 18 and in the discharge pipe 34, are monitored in a continuous manner by a control and activation unit 55, and the valve 21 is opened and closed as a function of their respective values. The first electromagnetic valve 35 is constantly open in order to permit the discharge of the dialysis liquid being prepared during the flushing procedure, and it is closed when the dialysis is in progress. The valves 32, 38 and 40 serve to close or open the corresponding pipes as a function of predetermined safety conditions. The control unit 55, which receives the pressures Pi and P0 measured by the sensors 20 and 37, controls all the valves of the circuit (in particular valve 21).

The flushing method proceeds as follows. To start with, the electromagnetic valve 21 is closed and the first valve 35 on the discharge pipe 34 is open. After the connection of the hydraulic circuit in the manner described and represented, the arterial pump 12 is started up and suctions the flushing liquid (physiological saline solution) from the bag 14 and forces it into the arterial line 11 and into the blood compartment 3 of the dialyser 2, as is represented by the arrows in FIG. 1. The liquid then flows into the venous line 15 and the pipe section 17 and enters the dialysis liquid compartment via the inlet 9. Thus, the flushing liquid circulates in the two compartments 3 and 4 of the dialyser in the same direction, from the bottom upwards, which facilitates the discharge of the air contained in the dialyser 2.

After the dialysis liquid compartment 4 has been flushed, the liquid flows into the connecting pipe 18, and this brings about an increase in the pressure in this pipe, the valve 21 being closed. When the pressure prevailing in the connecting pipe 18, as measured by the sensor 20, exceeds a predetermined threshold (for example 80 mmHg), the opening of the valve 21 is controlled by the unit 55. The flushing liquid then flows into the discharge pipe 35 where the pump 36 causes it to circulate with the dialysis liquid under preparation. Thereafter, the valve 21 remains activated as a function of the pressure, but its state (open/closed) no longer depends on the absolute value of the pressure in the connecting pipe 18: it is then a function of the pressure difference $\Delta P$ between the pressure Pi prevailing in the connecting pipe 18 and the pressure P0 prevailing in the discharge pipe 34, so that the flushing liquid flows permanently into the discharge pipe 34 (which eliminates the risk of the dialysis liquid under preparation coming into contact with the dialyser 2).

Figure 2:
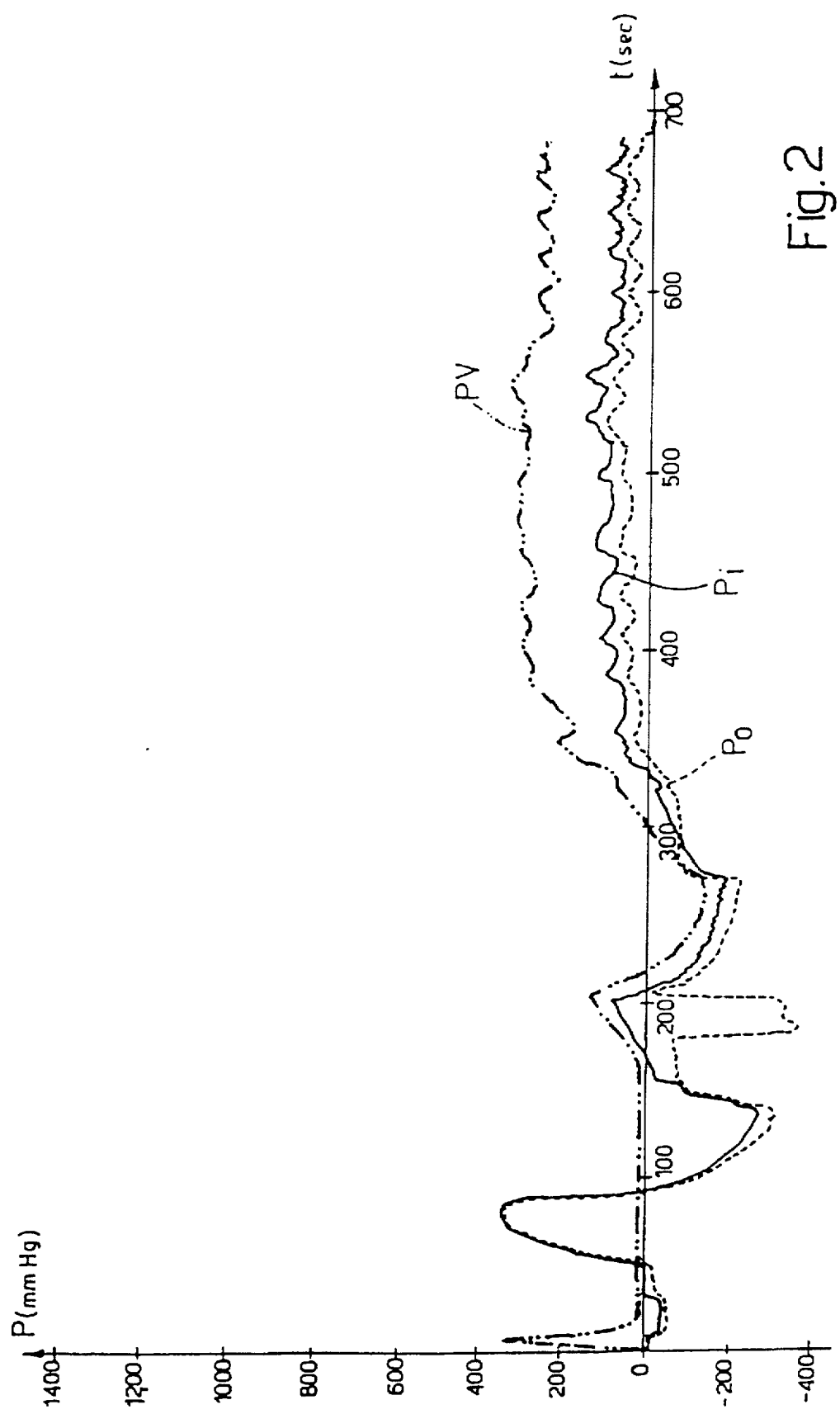
FIG. 2 illustrates the course of the curves for certain measured variables in the circuit in FIG. 1.

In practice, when $\Delta P=Pi-P0<30$ mmHg, the valve 21 is closed, and when $\Delta P>50$ mmHg, the valve 21 is opened. The curve of the pressures Pi and P0 in the tubes 18 and 34 resulting from this control can be seen in FIG. 2 where (starting from $t \approx 350$ s) one can see an undulating progression of the two pressures, due to the continuing opening and closing of the valve 21. FIG. 2 also shows the course of the pressure curve VP in the venous line 15.

Activating the valve 21 in the manner which has just been explained causes a series of pressure waves inside the dialyser 2, in the venous line 15 and in the connecting pipe 18, which facilitates the dislodging of the air bubbles, clinging to the membrane of the dialyser 2 and to the walls of the pipes, and their discharge.

At the end of the flushing procedure, the receptacle 14 is uncoupled from the arterial line 11, which can then be connected to the vascular circuit of a patient by means of a cannula. The pipe section 17 is disconnected from the dialyser 2 and is uncoupled from the venous line 15, which can then be connected to the vascular circuit of the patient by means of a cannula. The first valve 35 is closed, the connection piece 48 serving to connect the two sections of the discharge pipe 34 is opened, and the second section of the discharge pipe 34 is connected to the orifice of the dialysis liquid compartment to which the pipe section 17 was connected previously. In this way, during the dialysis session, the dialysis liquid issuing from the second chamber of the ultrafilter 22 flows into the connecting pipe 18, into the compartment 4 (in a direction counter to that of the arrow in FIG. 1) and into the discharge pipe 34.

The present invention is not limited to the embodiments which have been described and illustrated, and it is open to variations. In particular, the method which has been described can just as well be implemented when the flushing liquid is not discharged into the discharge pipe used for the dialysis liquid under preparation, and when two independent flushing circuits are used for flushing the two compartments of the dialyser. Moreover, the opening and closing of the valve 21 arranged on the connecting pipe can be controlled as a function of parameters other than the pressure prevailing in the pipes, in particular as a function of a predetermined time sequence, the valve 21 being opened and closed during predetermined time intervals.

What is claimed is:

1. A method for flushing a blood treatment apparatus, which has a first compartment and second compartment separated by a semi-permeable membrane, comprising the steps of:

setting up a flushing circuit by connecting an inlet of the blood treatment apparatus to a flushing liquid source, and an outlet of the blood treatment apparatus to discharge means;

circulating flushing liquid through the flushing circuit by running pumping means arranged in the flushing circuit; and causing pressure waves at time intervals in the flushing circuit by alternately opening and closing occlusions means arranged in the flushing circuit in order to dislodge air bubbles adhering to an inner wall of the blood treatment apparatus and to discharge these air bubbles in the flushing liquid.

2. A method according to claim 1, wherein the opening and closing of the occlusion means are controlled as a function of a pressure Pi measured in a flushing circuit section located between the pumping means and the occlusion means.

3. A method according to claim 1, wherein the opening and closing of the occlusion means are controlled in accordance with a predetermined time sequence.

4. A method according to claim 1, wherein the flushing circuit is set up by connecting an outlet of the first compartment to an inlet of the second compartment and by connecting an outlet of the second compartment to the discharge means.

5. A method according to claim 1, wherein the flushing circuit is set up by connecting an outlet of one of the first compartment and the second compartment to a discharge pipe of a treatment liquid generator.

6. A method according to claim 5, characterized in that:

a pressure P0 is measured in the discharge pipe;

the difference $\Delta P = Pi - P0$ of the pressures in the flushing circuit and in the discharge pipe is calculated; and the opening of the occlusion means is controlled when the pressure difference $\Delta P$ is greater than a first predetermined threshold value, and the closing of the occlusion means is controlled when the pressure difference $\Delta P$ is less than a second predetermined threshold value.

7. A device for flushing a blood treatment apparatus, which has a first compartment and second compartment separated by a semi-permeable membrane, the device comprising:

a flushing circuit connected to the blood treatment apparatus, the flushing circuit having supply means for supplying flushing liquid to the blood treatment apparatus and discharge means for discharging used flushing liquid from the blood treatment apparatus; and means for dislodging bubbles adhering to an inner wall of the blood treatment apparatus and discharging the bubbles in the flushing liquid, the means for dislodging bubbles comprising:

pumping means for circulating flushing liquid through the flushing circuit, occlusion means for selectively blocking the circulation of liquid in the flushing circuit; and control means for controlling an operation of the pumping means and the opening and closing of the occlusion means at time intervals in order to cause pressure waves in the flushing circuit.

8. A device according to claim 7, wherein the discharge means comprises a pipe connecting an outlet of the blood treatment apparatus to a discharge pipe of a treatment liquid generator.

9. A device according to claim 8, wherein the control means is programmed to control the opening and closing of the occlusion means in accordance with a predetermined time sequence.

10. A device according to claim 7, further comprising first pressure-measuring means for measuring the pressure Pi within a section of the flushing circuit situated between the pumping means and the occlusion means, and second pressure-measuring means for measuring the pressure P0 within the discharge pipe.

11. A device according to claim 10, wherein the control means are programmed to control the opening and closing of the occlusion means as a function of the pressures Pi and P0 measured by the first and second pressure-measuring means.

12. A device according to claim 11, wherein the control means is programmed to control the opening of the occlusion means when the pressure difference $Pi - P0 = \Delta P$ is greater than a first predetermined threshold value, and the closing of the occlusion means is controlled when the pressure difference $\Delta P$ is less than a second predetermined threshold value.

* * * * *